United States Patent [19]

Kellenberger et al.

[11] Patent Number: 5,149,335
[45] Date of Patent: Sep. 22, 1992

[54] ABSORBENT STRUCTURE

[75] Inventors: Stanley R. Kellenberger, Appleton; Wen-Huey Shih-Schroeder, Little Chute; Anthony J. Wisneski, Kimberly, all of Wis.

[73] Assignee: Kimberly-Clark Corporation, Neenah, Wis.

[21] Appl. No.: 484,598

[22] Filed: Feb. 23, 1990

[51] Int. Cl.⁵ .............................................. A61F 13/15
[52] U.S. Cl. .................................. 604/372; 604/358
[58] Field of Search ............. 604/365, 368, 378, 385.1

[56] References Cited

U.S. PATENT DOCUMENTS

| Re. 32,649 | 4/1988 | Brandt et al. | 604/368 |
|---|---|---|---|
| 2,331,271 | 10/1943 | Gilchrist | 128/284 |
| 2,952,260 | 9/1960 | Burgeni | 128/290 |
| 2,955,641 | 10/1960 | Burgeni | 154/33 |
| 3,017,304 | 1/1962 | Burgeni | 154/54 |
| 3,060,936 | 10/1962 | Burgeni | 128/290 |
| 3,070,095 | 12/1962 | Torr | 128/284 |
| 3,347,236 | 10/1967 | Torr | 128/284 |
| 3,494,362 | 2/1970 | Burgeni | 128/290 |
| 3,669,103 | 6/1972 | Harper et al. | 128/156 |
| 3,670,731 | 6/1972 | Harmon | 128/284 |
| 3,810,468 | 5/1974 | Harper et al. | 128/156 |
| 3,890,974 | 6/1975 | Kozak | 128/287 |
| 3,903,889 | 9/1975 | Torr | 128/287 |
| 3,926,891 | 12/1975 | Gross et al. | 260/29.6 E |
| 3,935,099 | 1/1976 | Weaver et al. | 210/43 |
| 3,954,721 | 5/1976 | Gross | 526/14 |
| 3,997,484 | 12/1976 | Weaver et al. | 260/17.4 GC |
| 4,055,180 | 10/1977 | Karami | 128/287 |
| 4,062,817 | 12/1977 | Westerman | 260/17.45 G |
| 4,069,177 | 1/1978 | Smith | 260/17.4 GC |
| 4,076,663 | 2/1978 | Masuda et al. | 260/17.4 GC |
| 4,090,013 | 5/1978 | Ganslaw et al. | 526/15 |
| 4,102,340 | 7/1978 | Mesek et al. | 128/287 |
| 4,103,062 | 7/1978 | Aberson et al. | 428/283 |
| 4,104,214 | 8/1978 | Meierhoefer | 260/17.4 CL |
| 4,105,033 | 8/1978 | Chatterjee et al. | 128/285 |
| 4,144,886 | 3/1979 | Holst et al. | 128/284 |
| 4,155,893 | 5/1979 | Fujimoto et al. | 260/29.6 H |
| 4,190,562 | 2/1980 | Westerman | 260/17.4 |
| 4,191,672 | 3/1980 | Salome et al. | 260/29.6 |
| 4,224,366 | 9/1980 | McCabe, Jr. | 428/72 |
| 4,242,408 | 12/1980 | Evani et al. | 428/290 |
| 4,260,443 | 4/1981 | Lindsey et al. | 156/220 |
| 4,269,188 | 5/1981 | Nishizawa et al. | 128/287 |
| 4,286,082 | 8/1981 | Tsubakimoto et al. | 526/240 |
| 4,327,728 | 5/1982 | Elias | 128/285 |
| 4,333,462 | 6/1982 | Holtman et al. | 128/287 |
| 4,333,463 | 6/1982 | Holtman et al. | 128/287 |
| 4,340,706 | 7/1982 | Obayaski et al. | 526/207 |

(List continued on next page.)

FOREIGN PATENT DOCUMENTS

| 0198683 | 10/1986 | European Pat. Off. |
| 0202125 | 11/1986 | European Pat. Off. |
| 0202127 | 11/1986 | European Pat. Off. |
| 0258120 | 3/1988 | European Pat. Off. |
| 0304319 | 2/1989 | European Pat. Off. |

(List continued on next page.)

Primary Examiner—David Isabella
Assistant Examiner—Gina M. Gualtieri
Attorney, Agent, or Firm—Thomas J. Mielke

[57] ABSTRACT

One aspect of the present invention relates to an absorbent structure and garment comprising a superabsorbent material having a free-swell rate of less than about 60 seconds and a five-minute AUL of at least 15 g/g. The superabsorbent material is contained by containment means, such as a fibrous matrix, such that the superabsorbent material is present in said absorbent structure in an amount of from about 60 to about 100 weight percent based on the total weight of the containment means and superabsorbent material.

A second aspect relates to an absorbent garment including containment means containing a high concentration of a superabsorbent material and defining a dry volume less than about 180 cubic centimeters. The absorbent garment has a saturated retention capacity of at least about two times the dry volume, and wherein the containment means and superabsorbent material account for at least about 60 volume percent of said saturated retention capacity.

58 Claims, 3 Drawing Sheets

U.S. PATENT DOCUMENTS

| | | | |
|---|---|---|---|
| 4,360,021 | 11/1982 | Stima | 128/287 |
| 4,381,782 | 5/1983 | Mazurak et al. | 604/368 |
| 4,381,783 | 5/1983 | Elias | 604/368 |
| 4,389,487 | 6/1983 | Ries | 435/273 |
| 4,397,644 | 8/1983 | Matthews et al. | 604/378 |
| 4,411,660 | 10/1983 | Dawn et al. | 604/396 |
| 4,414,255 | 11/1983 | Tokuyama et al. | 428/154 |
| 4,429,001 | 1/1984 | Kolpin et al. | 428/283 |
| 4,449,977 | 5/1984 | Korpman | 604/336 |
| 4,461,621 | 7/1984 | Karami et al. | 604/368 |
| 4,497,772 | 2/1985 | Cowling | 210/691 |
| 4,500,315 | 2/1985 | Pieniak et al. | 604/379 |
| 4,535,098 | 8/1985 | Evani et al. | 521/149 |
| 4,537,590 | 8/1985 | Pieniak et al. | 604/379 |
| 4,540,454 | 9/1985 | Pieniak et al. | 156/62.2 |
| 4,559,050 | 12/1985 | Iskra | 604/368 |
| 4,573,988 | 3/1986 | Pieniak et al. | 604/379 |
| 4,596,567 | 6/1986 | Iskra | 604/368 |
| 4,605,401 | 8/1986 | Chmelir et al. | 604/368 |
| 4,605,402 | 8/1986 | Iskra | 604/368 |
| 4,610,678 | 9/1986 | Weisman et al. | 604/368 |
| 4,650,479 | 3/1987 | Insley | 604/358 |
| 4,655,757 | 4/1987 | McFarland et al. | 604/366 |
| 4,666,975 | 5/1987 | Yamasaki et al. | 524/733 |
| 4,673,402 | 6/1987 | Weisman et al. | 604/368 |
| 4,699,619 | 10/1987 | Bernardin | 604/378 |
| 4,699,620 | 10/1987 | Bernardin | 604/385 A |
| 4,699,823 | 10/1987 | Kellenberger et al. | 428/219 |
| 4,742,086 | 5/1988 | Masamizu et al. | 521/62 |
| 4,755,178 | 7/1988 | Insley et al. | 604/367 |
| 4,773,903 | 9/1988 | Weisman et al. | 604/368 |
| 4,798,603 | 1/1989 | Meyer et al. | 604/378 |
| 4,833,222 | 5/1989 | Siddall et al. | 526/200 |
| 4,834,735 | 5/1989 | Alemany et al. | 604/368 |

FOREIGN PATENT DOCUMENTS

| | | |
|---|---|---|
| 0318989 | 6/1989 | European Pat. Off. . |
| 0336578 | 10/1989 | European Pat. Off. . |
| 2222780 | 11/1973 | Fed. Rep. of Germany . |
| 2293914 | 7/1976 | France . |
| 63-99861 | 5/1988 | Japan . |
| 2119384 | 11/1983 | United Kingdom . |
| 2155020 | 9/1985 | United Kingdom . |
| 2174037 | 10/1986 | United Kingdom . |

ABSORBENT STRUCTURE

BACKGROUND OF THE INVENTION

1. Field of the Invention

The present invention relates to absorbent structures and absorbent garments formed from the structures. Specifically, the present invention relates to absorbent structures comprising relatively high concentrations of a superabsorbent material and to absorbent garments which comprise relatively small absorbent structures.

2. Description of the Related Art

Absorbent structures suitable for use in absorbent garments such as diapers, adult incontinent products and the like are known. Such absorbent structures are described, for example, in U.S. Pat. No. 4,699,619 issued Oct. 13, 1987 to Bernardin; U.S. Pat. No. 4,798,603 issued Jan. 17, 1989 to Meyer et at.; and U.S. Pat. No. 4,834,735 issued May 30, 1989 to Alemany et al. Generally, such absorbent structures comprise a fibrous matrix and, optionally, a high-absorbency material. The fibrous matrix is suitable formed from airlaid cellulosic fibers such as those fibers commonly known as wood pulp fluff, or a coform material comprising cellulosic fibers and meltblown polyolefin fibers. A wide variety of high-absorbency materials are known to those skilled in the art. See, for example, U.S. Pat. Nos. 4,076,63 issued Feb. 28, 1978 to Masuda et al; 4,286,082 issued Aug. 25, 1981 to Tsubakimoto et al.; 4,062,817 issued Dec. 13, 1977 to Westerman; and 4,340,706 issued Jul. 20, 1982 to Obayashi.

Known absorbent structures generally comprise a relatively low amount (less than about 50 weight percent) of the high-absorbency material. There are several reasons for this. For example, high-absorbency materials employed in known absorbent structures have generally not had an absorption rate which would allow them to absorb liquid at the rate at which the liquid is applied to the absorbent structures during use. Accordingly, the fibrous matrix must serve as a reservoir which will hold the liquid discharged thereon until the liquid is absorbed by the high-absorbency material. Additionally, many of the known high-absorbency materials, particularly the synthetic high-absorbency materials, have exhibited gel blocking. Gel blocking refers to the situation wherein the particles of high-absorbency material deform during swelling and block the interstitial spaces between the particles or between the particles and the fibrous matrix thus preventing the flow of liquid through the interstitial spaces. At lower levels of addition the fibrous matrix serves to keep the particles of high-absorbency material separated from one another and provides a capillary structure which allows a liquid to pass through the fibrous matrix to reach high absorbency materials located remote from the point at which the liquid is applied to the absorbent structure.

Dispersing such high-absorbency materials in a fibrous matrix at relatively low concentrations in order to avoid gel blocking resulted in the need to locate high-absorbence materials in areas relatively remote from the point at which the liquid is applied to the absorbent structure. That is, in order to introduce useful amounts of high-absorbency material into an absorbent structure and yet disperse such high-absorbency materials sufficiently to prevent gel blocking, it was necessary for the absorbent structures to have relatively large surface areas and to be relatively thick.

Alternatively, it was necessary to design multi-component systems in an attempt to compensate for the problems associated with employing higher concentrations of high-absorbency material. See, for example, U.S. Pat. No. 4,673,402 issued Jun. 16, 1987 to Weisman et al. which describes a dual layered absorbent core. The upper layer is a fluid acquisition layer containing up to 8 percent of a high-absorbency material. The lower layer is a fluid storage layer containing up to 60 weight percent of a high-absorbency material. The upper layer is present to absorb and hold a liquid until the lower layer can absorb the liquid.

Since a liquid to be absorbed by an absorbent structure is generally applied to the structure in a relatively localized area, it became necessary to devise ways in which to move the liquid to be absorbed from the point of application to remote areas of the absorbent structure for absorption by the high-absorbency materials. This need precipitated the use of various structures and methods which are described as being capable of distributing a liquid throughout the absorbent structure. See, for example. U.S. Pat. No. 4,699,619 issued Oct. 13, 1987, to Bernardin; U.S. Pat. Nos. 2,952,260, 2,955,641, 3,017,304, 3,060,936, and 3,494,362 to Burgeni; U.S. Pat. No. 4,103,062 to Aberson; and U.S. Pat. No. 4,397,644 to Matthews et al. Use of such structures and methods further contributed to the size and thickness of the absorbent structures.

Prior to the use of high-absorbency materials in absorbent structures, it was general practice to form absorbent structures such as those suitable for use in infant diapers, entirely from wood pulp fluff. Given the relatively low amount of liquid absorbed by wood pulp fluff on a gram of liquid absorbed per gram of wood pulp fluff (about 7-9 g/g saturated retention capacity), it was necessary to employ relatively large quantities of wood pulp fluff, thus necessitating the use of relatively large, thick absorbent structures. The introduction of high-absorbency materials into such structures allowed for the use of less wood pulp fluff, since the high-absorbency material has a significantly higher absorption capacity on a gram per gram basis (at least about 15 g/g saturated retention capacity). Moreover, such high-absorbency materials are less pressure sensitive than wood pulp fluff. Thus, the use of the high-absorbency materials allowed for the production and use of a smaller, thinner absorbent structure. Nonetheless, for the above reasons, it was still necessary to use relatively low concentrations of superabsorbent material and enough fibrous matrix to permit the high-absorbency materials to function in the desired manner.

It is generally desired that absorbent garments such as diapers be able to rapidly absorb multiple insults of urine during use. Typically, diapers have been produce with absorbent capacities greater than the actual in-use needed capacity. This surplus capacity was believed necessary to achieve the desired performance (lack of leakage or low level of skin wetness) by the diapers. For example, if it was anticipated that a given diaper needed to be able to absorb 250 milliliters of urine in-use, the diaper may have been designed with an absorbent capacity of 400 milliliters or more. The excess capacity was necessary to compensate for the inability of the absorbent medium to absorb the urine at in-use delivery rates and under in-use delivery conditions. The practice of building in excess absorbent capacity is inefficient and undesirable.

SUMMARY OF THE INVENTION

It is desirable to produce an absorbent structure able to meet or exceed the performance characteristics of known absorbent structures while containing a relatively high concentration of high-absorbency material. It is also desired to produce an absorbent structure which is able to rapidly absorb a discharged liquid under pressures typically encountered during use and to retain the absorbed liquid under pressures typically encountered during use. Further, it is desired to produce an absorbent structure which has a lower volume and mass than known absorbent structures while having generally the same absorbent capacity as the known absorbent structures thus, allowing for easier, more efficient disposal.

These and other related goals are achieved in an absorbent structure comprising means for containing a superabsorbent material (containment means) and a superabsorbent material contained by the means. The superabsorbent material has a free-swell rate of less than about 60 seconds, and a five-minute absorbency under load (AUL) of at least about 15 g/g. Moreover, the superabsorbent material is present in the containment means in an amount of from about 60 to about 100 weight percent, based on the total weight of the containment means and the superabsorbent material. The described combination of free-swell rate and five-minute AUL may allow the superabsorbent material to absorb a liquid discharged thereon at substantially the rate of discharge encountered during use of the absorbent structure in an absorbent garment, and to maintain sufficient structural integrity of the swollen superabsorbent material to allow a discharged liquid to pass through the absorbent structure despite the high concentration of superabsorbent material.

In another aspect, it is desirable to provide a thin, absorbent garment, such as an infant diaper, which garment employs an absorbent structure having a relatively small volume and high concentration of superabsorbent material. Further, it is desirable to provide an absorbent garment which has a relatively small volume and a relatively high capacity.

In one embodiment, these goals are achieved in absorbent garment comprising an absorbent structure which absorbent structure comprises means for containing a superabsorbent material (containment means) and a superabsorbent material contained by the containment means. The superabsorbent material has a free-swell rate of less than about 60 seconds, and a five-minute AUL of at least about 15 g/g. Moreover, the superabsorbent is present in the containment means in an amount of from about 60 to about 100 weight percent, based on the total weight of the containment means and the superabsorbent material.

In another embodiment, this goal is achieved in an absorbent garment having a saturated retention capacity, the absorbent garment comprising means for containing a superabsorbent material and a superabsorbent material contained by the containment means. The superabsorbent material is present in the containment means in an amount of from about 60 to about 100 weight percent based on total weight of the containment means and the superabsorbent material. The containment means and the superabsorbent material define a total dry volume of less than about 180 cubic centimeters and account for at least about 60 volume percent of the saturated retention capacity of the absorbent garment. The absorbent garment has a saturated retention capacity which is at least about twice the total dry volume defined by the containment means and the superabsorbent material.

DETAILED DESCRIPTION OF THE PREFERRED EMBODIMENT

Figure 1:
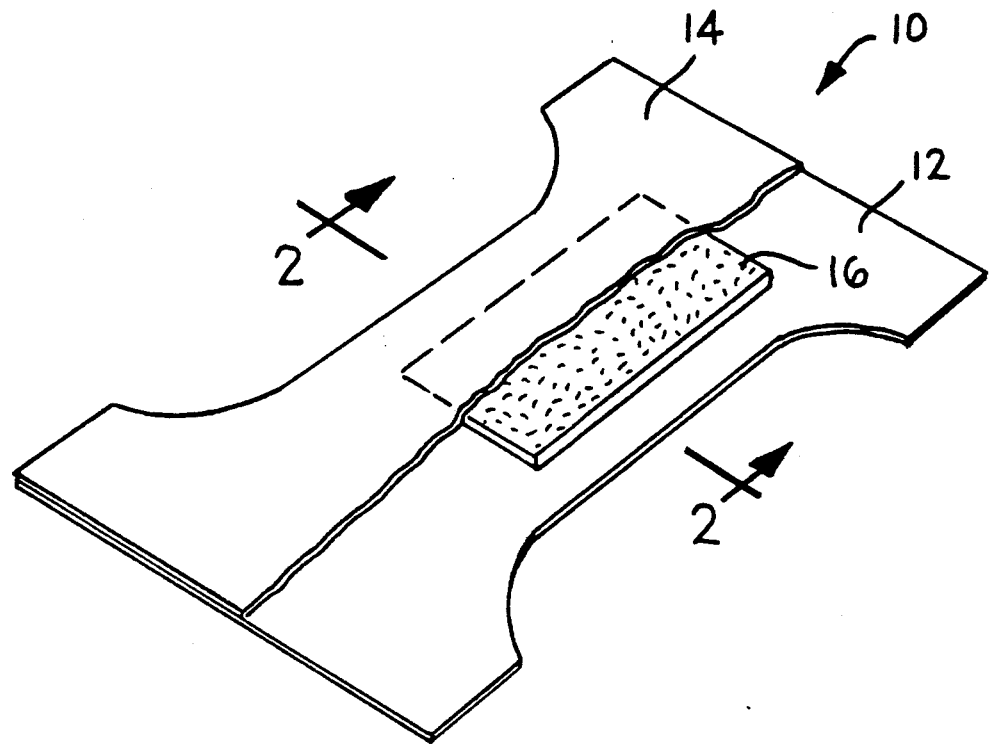
FIG. 1 is a perspective view of one embodiment of a disposable diaper according to the present invention.

In one aspect, the present invention concerns an absorbent structure and an absorbent garment possessing improved, desirable characteristics achievable by the careful selection and use of the superabsorbent material employed in forming such absorbent structures and absorbent garments.

Specifically, in one aspect, the present invention concerns an absorbent structure comprising means for containing a superabsorbent material and a superabsorbent material. As used herein, superabsorbent material refers to a water-swellable, substantially water-insoluble organic or inorganic material capable of absorbing at least about 10 times its weight and preferably at least about 15 times its weight in an aqueous solution containing 0.9 weight percent of sodium chloride.

Organic material suitable for use as a superabsorbent material of the present invention can include natural materials such as agar, pectin, guar gum, and the like, as well as synthetic materials, such as synthetic hydrogel polymers. Such hydrogel polymers include, for example, alkali metal salts of polyacrylic acids; polyacrylamides; polyvinyl alcohol; ethylene maleic anhydride copolymers; polyvinyl ethers; hydroxypropylcellulose; polyvinyl morpholinone; polymers and copolymers of vinyl sulfonic acid, polyacrylates, polyacrylamides, polyvinyl pyridine; and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water-insoluble. Crosslinking may, for example, be by irradiation or by covalent, ionic, Van der Wall, or hydrogen bonding. The superabsorbent materials may be in any form suitable for use in absorbent structures, including, particles, fibers, flakes, spheres, and the like. In one preferred embodiment of the present invention, the superabsorbent material comprises particles of a hydrocolloid, preferably an ionic hydrocolloid.

While a wide variety of superabsorbent materials are known, the present invention relates, in one aspect, to the proper selection of superabsorbent materials and to the use of such materials in the proper way to allow formation of the improved absorbent structures and garments described herein. More specifically, the superabsorbent materials are selected so that they are capable of rapidly absorbing a liquid such as urine. Preferably, the superabsorbent materials are capable of absorbing urine at substantially the same rate urine as applied to the superabsorbent materials during use. Moreover, the superabsorbent materials have the ability to absorb such liquids under an applied load.

For the purposes of this application, a superabsorbent material having a saturated retention capacity, as defined and determined below, of greater than 30 grams per gram will be deemed to be capable of rapidly absorbing liquids when one gram of the superabsorbent material is able to absorb about 30 milliliters of an aqueous solution containing 0.9 weight percent of sodium chloride in less than about 60 seconds, preferably in less than about 40 seconds, and most preferably in less than about 30 seconds. The number of seconds required for one gram of a superabsorbent material, having a saturated retention capacity greater than 30 grams per gram, to absorb about 30 milliliters of an aqueous solution containing 0.9 weight percent of sodium chloride is referred to herein as the free-swell rate.

A superabsorbent material having a saturated retention capacity, as defined and determined below, of less than 30 grams per gram will be deemed to be capable of rapidly absorbing liquids when one gram of the superabsorbent material is able to absorb an amount of an aqueous solution containing 0.9 weight percent of sodium chloride, equal to its saturated retention capacity in less than about 60 seconds, preferably in less than about 40 seconds, and most preferably in less than about 30 seconds. The number of seconds required for one gram of a superabsorbent material, having a saturated retention capacity less than 30 grams per gram, to absorb an amount of an aqueous solution containing 0.9 weight percent of sodium chloride equal to its saturated retention capacity is referred to herein as the free-swell rate. The exact method by which the free-swell rate is determined is set forth in detail below in connection with the examples.

Additionally, the superabsorbent material employed in the absorbent structures of the present invention must be able to absorb a liquid under an applied load. For the purposes of this application, the ability of a superabsorbent material to absorb a liquid under an applied load and thereby perform work is quantified as the absorbency under load (AUL). The AUL value is expressed as the amount (in milliliters) of an aqueous 0.9 weight percent sodium chloride solution which the superabsorbent material can absorb per gram of superabsorbent material in five-minutes under a load of 2.0 kilopascals (approximately 0.3 pounds per square inch) while restrained from swelling in the plane normal to the applied load. The method by which the five-minute AUL is determined is set forth in detail below in connection with the examples which follow.

Superabsorbent materials will be deemed to have the desired ability to absorb a liquid under an applied load when they have a five-minute AUL value of at least about 15 g/g, preferably, at least about 18 g/g and most preferably at least about 21 g/g. The five-minute AUL value of a particular superabsorbent material is hypothesized, without intending to be limited by the hypothesis, to be important for the following reason. Particles of superabsorbent materials which do not have the required five-minute AUL value generally form relatively soft gelatinous masses upon absorption of a liquid. This results in few or no interstitial spaces between the particles of superabsorbent material. Superabsorbent materials which, in particulate form, have the required five-minute AUL value are generally capable of absorbing a liquid under a load while maintaining interstitial spaces between the particles of superabsorbent material. In this manner, a liquid to be absorbed can flow through the interstitial spaces of the swollen superabsorbent material due to capillary action in order to quickly contact unswollen or partially swollen particles of superabsorbent material. Because of this, maximum utilization of the superabsorbent material is more quickly achieved. If the interstitial spaces are filled by the expanding superabsorbent material, liquid subsequently applied thereto cannot move quickly through the interstitial spaces to be absorbed by the superabsorbent material. Instead, the liquid must diffuse through the already swollen particles of superabsorbent material to reach and be absorbed by the unswollen or partially swollen particles of superabsorbent material.

Additionally, it is desired that the superabsorbent material have the stated five-minute AUL in order for the superabsorbent material to absorb a liquid under normal pressures applied to such superabsorbent material when present in an absorbent garment such as an infant diaper or the like.

Exemplary of a specific superabsorbent material suitable for use in the present invention is a polyacrylate material, commercially available from Norsolor Company (a division of ORKEM) of France, under the trade designation Norsacryl TM B41S. Also suitable for use as the superabsorbent materials of the present invention are generally non-friable (when wet or dry) particles of agglomerated fines of a water-swellable, substantially water-insoluble polyacrylic acid superabsorbents the fines of which can be obtained from, for example, the Dow Chemical Company under the trade designation Drytech TM or Stockhausen U.S.A. under the trade designation Favor TM SAB. The particles of agglomerated fines can generally be prepared by suspending the fines in an inert hydrophobic liquid and adding to the particles, slowly, under polymerization conditions, an aqueous solution or mixture such that agglomerates are formed. The aqueous solution or mixture preferably comprises at least one ethylenically unsaturated carboxylic acid which is polymerizable with the polymeric fines and an amorphous, oil dispersible, substantially water-insoluble, particulate material. A cross-linking agent may be added to the aqueous solution or mixture. Similarly, a hydrophilizing agent may be added to ensure all surfaces are wettable especially the interstitial spaces formed by the agglomerated particles. Such a method is described in detail in copending U.S. patent application Ser. No. 07/304,616 filed Jan. 24, 1989, assigned to the Dow Chemical Company and entitled "Aggregates of Water-Swellable Polymers and a Method for Producing Aggregates of Water-Swellable Polymers, the Aggregates Having Increased Hydration Rate Over Unassociated Water-Swellable Polymers" which is incorporated herein by reference. This method and the superabsorbent polymer particles produced therefrom are described as follows.

The water-swellable or lightly crosslinked hydrophilic polymer particles useful in the present invention can be any of the known hydrophilic polymers which are capable of absorbing large quantities of fluids. Examples of such polymers include those disclosed in U.S. Pat. Nos. 3,926,891 issued Dec. 16, 1975, to Gross et al.; 3,935,099 issued Jan. 27, 1976, to Weaver et al; 3,997,484 issued Dec. 14, 1976, to Weaver et al.; 4,090,013 issued May 16, 1978, to Ganslaw et al.; 4,190,562 issued Feb.

26, 1980, to Westerman et al.; and 4,833,222 issued May 23, 1989, to Siddall et al. Such hydrophilic polymers are prepared from water-soluble alpha,beta-ethylenically unsaturated monomers such as mono- and polycarboxylic acids and acrylamide and its derivatives.

The water-soluble monomers which are polymerized to form the water-swellable polymers of the present invention include those monomers listed in U.S. Pat. Nos. 4,833,222 issued May 23, 1989, to Siddall et al. Examples of such monomers include alpha,beta-ethylenically unsaturated monomers such as mono- and polycarboxylic acids.

The water-swellable or lightly crosslinked hydrophilic polymer particles which benefit the greatest from being incorporated into the aggregates or clusters of the present invention are those unassociated particles which have a mesh size of less than 400 mesh (37 micrometers) and preferably from 170 to 400 mesh (88 to 37 micrometers).

The aggregates of water-swellable polymers are comprised of water-swellable polymer particles associated by being bound to other water-swellable polymer particles in a random packing configuration spatially distributed to allow aqueous absorption.

The aqueous solution can be (a) water or (b) an ethylenically unsaturated monomer dispersed in water. When the aqueous solution comprises an ethylenically unsaturated carboxylic acid monomer, the monomer is polymerizable with the water-swellable polymer of the present invention and includes all of those monomers described above as water-soluble monomers particularly acrylic acid, methacrylic acid, crotonic acid, and isocrotonic acid, alkali metal salts and ammonium salts thereof. Suitable polycarboxylic acids include maleic acid, fumaric acid, and itaconic acid. Suitable acrylamide derivatives include methacrylamide. The preferred monomers include acrylic acid and methacrylic acid and their respective salt forms such as alkali metal or ammonium salts.

Optionally a crosslinking monomer can be added to the aqueous solution. Organic compounds having two or more ethylenic groups copolymerizable with the water-soluble monomers can be used as the crosslinking monomers. Exemplary crosslinking monomers include diacrylate or dimethacrylate of ethylene glycol, diethylene glycol, triethylene glycol, propylene glycol, 1,4-butanediol, 1,5-pentanediol, 1,6-hexanediol, neopentyl glycol, trimethylolpropane and pentaerythritol; triacrylates or trimethacrylates of trimethylolpropane and pentaerythritol; tetracrylates or tetramethacrylates of pentaerythritol, N,N'-methylene-bis-acrylamide, N,N'-methylene-bis-methacrylamide and triallylisocyanurate and the like. The preferred crosslinking monomer for the present invention is trimethylolpropanetriacrylate. The particulate material can also be present in the aqueous solution or can be present in the polymer particle suspension as discussed below.

Optionally, minor amounts of other water-soluble, unsaturated monomers may be present in the aqueous solution such as alkyl esters of the acid monomers. For example, methyl acrylate or methyl methacrylate may be present.

The inert hydrophobic liquid used to suspend the water-swellable polymer particles and the aqueous solution of monomer is usually an organic compound which is normally liquid at the conditions at which the polymerization process occurs. Operable liquids include hydrocarbons or substituted hydrocarbons. Preferred organic liquids are the halogenated hydrocarbons such as perchloroethylene, methylene chloride and the like, as well as liquid hydrocarbon having from 4 to 15 carbons per molecule including aromatic and aliphatic hydrocarbons and mixtures thereof, e.g., benzene, xylene, toluene, mineral oils, liquid paraffins such as kerosene, naphtha and the like. Of the foregoing organic liquids, the hydrocarbons are the more preferred, with aliphatic hydrocarbons being most preferred.

The particulate material comprising a hydrophobic character is an amorphous, highly oil-dispersible, approximately micrometer and sub-micrometer size, substantially water-insoluble particulate material. Typically, the size of the particulate material ranges from less than 1 to several micrometers in diameter. The particulate material is most preferably hydrophobic silicon dioxide, for example, the particulate material provided by the reaction of silica with polydimethyldichlorosilane. Other useful particulate materials include hydrophobic clays such as the cationic surfactant treated bentonite clays. An example of a hydrophobic clay is sold commercially as Bentone ® by N.L. Industries.

Preparing the aggregates or clusters requires suspending the aqueous absorbing polymer particles in the inert hydrophobic liquid. Typically, the weight ratio of polymer to liquid is not critical, however, for practical purposes the preferred ratio is in the range of from 1 to 10 to 10 to 1.

The aqueous solution can be water or can include an ethylenically unsaturated monomer. The ethylenically unsaturated monomer solution is typically prepared by first dispersing the monomer in water. The monomer can be preneutralized and exist as a salt or as a mixture of the acid and the salt, however if the monomer is in acidic form, the pH of the solution should then be adjusted to between 4 and 7. The weight ratio of monomer is typically 1:10 to 5:10 monomer to polymer particles. Preferably the weight ratio of monomer to polymer particles is typically 2:10, and the ratio of monomer to water it typically 0:10 preferably 4:10. Optionally, the aqueous solution (with or without the monomer) may also contain a crosslinker, chelating agent and initiator. Therefore, the total monomer, if present, is present in the range of 15 to 45 weight percent based on total weight of the solution. The crosslinker is typically added in an amount of 0 to 5 weight percent based on the total weight of the monomer.

The amorphous highly oil dispersible substantially water-insoluble particulate material is suspended in an inert hydrophobic liquid. The aqueous solution or aqueous monomer solution is then added to the particulate material to form a suspension of aqueous droplets or aqueous monomer droplets. The aqueous suspension or aqueous monomer suspension is then added slowly to the suspended polymer particles while the polymer particle solution is agitated and exposed to polymerization conditions. The polymerization temperature can range from 10° C. to 100° C., depending upon initiators chosen.

The size of the aggregates or clusters formed will depend on the size of the polymer particles with which the process begins. However, the major contributor to the size of the aggregates is the size of the droplets of hydrophobic liquid and then added to the suspended particles solution. The droplet size is controlled by the amount of amorphous highly oil dispersible substantially water-insoluble particulate material present in the monomer solution. For example, an aggregate of approximately 1000 micrometers can be formed when the droplets are approximately 50 micrometers in diameter. This is achieved if the particulate material is present in a ratio of approximately 0.3 to 2 percent based on the weight of total polymer present.

The aggregates or clusters can be filtered from the inert liquid, dried in an oven and crushed to a desirable size. The wetting agent can be added after the aggregates have been dried. Most economically, however, the wetting agent can be added after polymerization, but prior to drying, to allow for a single drying step of the polymer.

A wetting agent is defined as an agent which further improves the hydration rate of the polymer and does not reduce the surface tension of a supernate (provided by a standard test method) below 56 dynes/cm. The "standard test method" employed herein requires (1) treating dry polymer with 0.4 weight percent (based on dry weight of polymer) of polyol; (2) dissolving 1 g of the treated polymer in 150 g of 0.9 percent saline solution; (3) filtering off the supernate; and (4) determining the surface tension of the supernate. The surface tension is determined using a duNouy surface tension apparatus.

Ideally, the hydration rate of the polymer is improved without significantly reducing the absorbency properties of the aqueous fluid absorbent material in which the polymer is incorporated. Therefore, examples of such a wetting agent are non-surfactant or non-detergent type wetting agents such as polyols. Voranol ® (from The Dow Chemical Company) brand wetting agent is a preferred example of such a polyol.

Typically, the wetting agent is introduced to the polymer aggregates as an aqueous solution in an amount sufficient to increase the hydration rate of the polymer as compared to a polymer not treated with the wetting agent. Preferably, an amount of 0.2 to 2.0 weight percent of wetting agent, based on the weight of polymer, will be a sufficient amount. Most preferably, the amount of the wetting agent is 0.4 to 0.5 weight percent of the weight of polymer.

Illustrative methods of preparing these aggregated particles of superabsorbent polymers may be found in Appendix A.

If the polymer aggregates are dried and then surface treated with the wetting agent aqueous solution, the process entails several energy and time consuming steps. The polymer requires drying off the oil phase and water phase, then spraying the wetting agent solution on the polymer and finally redrying the polymer.

However, the intermediate drying step can be substantially reduced if after the polymerization is complete, the water is removed from the suspension, leaving the oil phase remaining with the polymer. A wetting agent in an aqueous solution is then added. Preferably the solution is added to the polymer aggregates slowly; most preferably the addition occurs over a period of from about 10 to about 30 minutes. The water can then be vacuum stripped and the oil can be removed by filtration or centrifugation. A final drying yields polymer aggregates having an improved hydration rate over polymer aggregates which have not been treated with the wetting agent.

Other methods believed suitable for forming the superabsorbent materials of the present invention are described in European Patent Application 0 318 989 published Dec. 1, 1988, and commonly assigned U.S. patent application Ser. No. 07/359,470 filed May 31, 1989, which are incorporated herein by reference.

In one preferred embodiment of the present invention, the superabsorbent material is in the form of particles which, in the unswollen state, have maximum cross-sectional diameters within the range of from about 50 microns to about 1000 microns, preferably within the range of from about 100 microns to about 800 microns, as determined by sieve analysis according to American Society for Testing and Materials (ASTM) test method D-1921. It is understood that the particles of superabsorbent material falling within the ranges described above, may comprise solid particles, porous particles or may be agglomerated particles comprising many smaller particles agglomerated into particles falling within the described size ranges. Superabsorbent material preferred for use in the present invention is generally characterized as having a relatively large surface area to weight ratio and is preferably formed by agglomerating smaller particles into particles having the preferred dimensions discussed above.

Superabsorbent materials having the particular free-swell rates and five-minute AUL values described above are capable of producing improved absorbent structures. This improvement stems, in one aspect, from the fact that superabsorbent materials having the described free-swell rate and five-minute AUL can be employed in absorbent structures in concentrations greater than possible with superabsorbent materials not possessing the stated free-swell rate and five-minute AUL values while still maintaining the desirable absorption characteristics of the absorbent structures.

In addition to the superabsorbent materials described above, the absorbent structures according to the present invention must comprise means to contain the superabsorbent material. Any means capable of containing the described superabsorbent materials, which means is further capable of being positioned in a device such as an absorbent garment, is suitable for use in the present invention. Many such containment means are known to those skilled in the art. For example, the containment means may comprise a fibrous matrix such as an airlaid or wetlaid web of cellulosic fibers, a meltblown web of synthetic polymeric fibers, a spunbonded web of synthetic polymeric fibers, a coformed matrix comprising cellulosic fibers and fibers formed from a synthetic polymeric material, airlaid heat-fused webs of synthetic polymeric material, open-celled foams, and the like. In one embodiment, it is preferred that the fibrous matrix comprise less than 10 preferably less than 5 weight percent of cellulosic fibers.

Alternatively, the containment means may comprise two layers of material which are joined together to form a compartment, which compartment contains the superabsorbent material. In such a case, at least one of the layers of material should be water-pervious. The second layer of material may be water-pervious or water-impervious. The layers of material may be cloth-like wovens or nonwovens, closed or open celled foams, perforated films, or may be fibrous webs of material. When the containment means comprises layers of material, the material should have a pore structure small enough or tortuous enough to contain the majority of the superabsorbent material.

Further, the containment means may comprise a support structure, such as a polymeric film, on which the superabsorbent material is affixed. The superabsorbent material may be affixed to one or both sides of the support structure which may be water-pervious or water-impervious.

In one preferred embodiment of the present invention, the inventors have discovered that when the containment means comprises a meltblown web of synthetic polymeric fibers, it is desirable that the meltblown fibers be hydrophilic. Synthetic polymeric fibers will be considered to be hydrophilic when the fibers have a contact angle of water in air of less than 90 degrees. For the purposes of this application, contact angle measurements are determined as set forth by Good and Stromberg in "Surface and Colloid Science" Vol. II (Plenum Press, 1979). The fibers may be rendered hydrophilic by using a hydrophilic polymeric material to form such fibers or, by treating generally hydrophobic fibers with a surface treatment which renders the fibers hydrophilic.

Specifically, hydrophilic fibers can be formed from an intrinsically hydrophilic polymer such as a block copolymer of nylon, e.g., nylon-6, and a polyethylene oxide diamine. Such block copolymers are commercially available from Allied-Signal Inc. under the trade designation Hydrofil ™. The hydrophilic fiber may also be formed from a water-swellable, substantially water-insoluble superabsorbent polymeric material such as a thermoplastic material described in U.S. Pat. No. 4,767,825 issued Aug. 30, 1988, to Pazos, et al., which is hereby incorporated by reference. Alternatively, the meltblown fibers may be formed from an intrinsically hydrophobic polymer such as a polyolefin or polyester which has been surface modified to provide a generally nonfugitive hydrophilic surface. Such a surface modified polyethylene is commercially available from the Dow Chemical Company under the trade designation Aspun ™ wettable polyethylene.

When the hydrophilic fibers are formed by applying a hydrophilic surface treatment to a generally hydrophobic polymer, it is believed desirable to employ a generally non-fugitive surface treatment in order to obtain the desired performance standards. Absorbent structures employed in absorbent garments such as diapers are often subjected to multiple insults of urine, if the surface treatment is fugitive it may be washed off with the initial insult thus, exposing the hydrophobic fiber surface. The hydrophobic fiber surface may impede the absorption performance of the absorbent structure. Of course, there are instances where hydrophobic fibers may be employed, particularly at lower concentrations of fiber and higher concentrations of superabsorbent material.

In another preferred embodiment, wherein the containment means comprises two layers of material which layers are joined to form a compartment adapted to contain the superabsorbent material, the two layers are suitably formed from any material capable of containing the superabsorbent material including woven and nonwoven material such as airlaid or wetlaid fibers, meltblown fibers, spunbonded fibers, coformed fibers and the like, and are joined to form a compartment by heat fusion, sonic bonding, adhesives, and the like. Clearly, a wide variety of materials may be employed to form the two layers and to join the layers together to form the compartment.

As indicated above, because the superabsorbent material has the described combination of free-swell rate and five-minute AUL, and does not need to be maintained in a fibrous matrix at relatively low degrees of concentration in order to avoid gel blocking, the described superabsorbent materials can be present in the absorbent structures in relatively high concentrations compared to known absorbent structures. Specifically, the absorbent structures according to the present invention suitably comprise at least about 60 to about 100 weight percent of superabsorbent material based on total weight of the containment means and the superabsorbent material. Preferably, the absorbent structures comprise from about 70 to about 100 weight percent of superabsorbent material based on total weight of the containment means and the superabsorbent material. Most preferably, the absorbent structures comprises from about 75 to about 99 weight percent of superabsorbent material based on total weight of the containment means and the superabsorbent material.

Superabsorbent materials not having the stated free-swell rate and five-minute AUL values are commonly employed by dispersing the superabsorbent materials in a fibrous matrix such as wood pulp fluff. Such superabsorbent materials are commonly dispersed at levels of about 50 weight percent or less. Use of superabsorbents in concentrations greater than about 50 weight percent is often described as being undesirable. Applicants have discovered, in one aspect, that superabsorbent materials having the described free-swell rate and AUL perform better at higher concentrations (greater than about 60 weight percent) than do superabsorbent materials having either a high free-swell rate and low AUL or a high AUL and low free-swell rate. At lower concentrations (less than about 50 weight percent) no significant improvement is seen in employing the high free-swell rate, high AUL superabsorbent materials compared to previously described high AUL, low free-swell rate superabsorbent materials such as those described in European Patent Publication No. 0 339 461, published Nov. 2, 1989.

Because the superabsorbent materials present in the absorbent structures of the present invention can be present in high concentrations, the absorbent structures of the present invention can be relatively thin and have a relatively small volume and still function in a desirable manner. Suitably, the absorbent structures according to the present invention have an average thickness of less than about 0.2 inches (5.1 millimeters), preferably less than about 0.15 inches (3.8 millimeters). Moreover, the absorbent structures suitably define a major planar surface having a surface area less than about 75 square inches (484 square centimeters), preferably less than about 50 square inches (323 square centimeters) and most preferably less than about 40 square inches (258 square centimeters).

As used herein, reference to the average thickness of an absorbent structure is intended to refer to the average of a number of thickness measurements taken under an applied load of about 0.2 pounds per square inch. The number of thickness measurements taken is sufficient to represent the average thickness of the entire absorbent structure.

The absorbent structures of the present invention are desirably relatively flexible to enhance comfort during use. For the purposes of this invention, such absorbent structures will be considered to possess the desired degree of flexibility when they have a Gurley stiffness value of less than about 2 grams, preferably less than about 1 gram.

The absorbent structures according to the present invention are suited to absorb many fluids including body fluids such as urine, menses, and blood and are suited for use in absorbent garments such as diapers, adult incontinent products, bed pads, and the like; in catamenial devices such as sanitary napkins, tampons, and the like; and in other absorbent products such as wipes, bibs, wound dressings and the like. Accordingly, in another aspect, the present invention relates to an absorbent garment comprising an absorbent structure as described above.

Use of the described absorbent structures in absorbent garments, allows for the formation of an absorbent garment which is able to rapidly receive a discharged liquid and yet which garment is thin. The average thickness of an absorbent garment according to this aspect of the invention is defined as the average thickness of the garment in the area of the garment which is coextensive with the absorbent structure contained thereon. The average thickness is determined as set forth above in connection with determining the average thickness of the absorbent structure, except that the absorbent garment is employed rather than just the absorbent structure.

Absorbent garments according to this aspect of the present invention suitably have an average thickness of less than about 0.25 inch (6.4 millimeters) preferably, less than about 0.22 inch (5.6 millimeters), and most preferably less than about 0.20 inch (5.1 millimeters).

In another aspect, the present invention relates to an absorbent garment which absorbent garment comprises means for containing a superabsorbent material and superabsorbent material contained by the means. The superabsorbent material is present in the containment means in an amount of from about 60 to about 100 weight percent, preferably from about 70 to about 100 weight percent, and most preferably from about 75 to about 99 weight percent, based on total weight of the containment means and superabsorbent material. The containment means and superabsorbent material define a total dry volume of less than about 180 cubic centimeters, preferably less than about 150 cubic centimeters, more preferably less than about 120 cubic centimeters and most preferably less than about 100 cubic centimeters. The absorbent garment has a saturated retention capacity which is at least about two times, preferably at least about 3 times, and most preferably at least about 5 times the dry volume of the containment means and superabsorbent material. The containment means and superabsorbent material account for at least about 60 volume percent, preferably at least about 75 volume percent, and most preferably at least about 85 volume percent of the saturated retention capacity of the absorbent garment. The method of determining the saturated retention capacity of the absorbent garment and the containment means and superabsorbent material is set forth below in connection with the examples.

Absorbent garments according to this aspect of the present invention employ a containment means and superabsorbent material which allows the garment to have a low total volume. The ability to produce a low total volume absorbent garment is desirable because disposal of the used garment is more efficient. Additionally, the absorbent garments may be thin, having an average thickness (as described above for absorbent garments) of less than about 0.25 inch (6.4 millimeters) preferably, less than about 0.2 inch (5.1 millimeters). A thin, low volume absorbent garment such as a diaper, may have a better fit when placed on a child, which better fit may allow the child to move about more easily.

Containment means and superabsorbent materials suitable for use in this aspect of the present invention are those containment means and superabsorbent materials generally described above in connection with the other aspects of the instant invention. However, the superabsorbent materials suitable for use in this aspect of the present invention are not limited to those described superabsorbents having the recited free-swell rates and five-minutes AUL values. Nonetheless, it is believed that superabsorbent materials having the recited free-swell rates and five-minute AUL values may represent the superabsorbent materials preferred for use in this aspect of the present invention.

Absorbent garments and structures according to all aspects of the present invention are generally subjected, during use, to multiple insults of a body fluid. Accordingly, the absorbent garments and structures are desirably capable of absorbing multiple insults of body fluids in quantities to which the absorbent garments and structures will be exposed during use. The insults are generally separated from one another by a period of time. When the absorbent garments and structures of the present invention have saturated retention capacities of at least 300 grams, they will be considered capable of absorbing such multiple insults when they have fluid uptake value of less than about 30 seconds preferably less than about 20 seconds.

As used herein, fluid uptake values are determined by subjecting the object to be tested to three insults of 100 milliliters of synthetic urine. The insults are applied to the object at a localized area at delivery rates of about 15 milliliters per second. The insults are spaced from one another by a period of about 5 minutes. The time required for the object to absorb each individual insult is notes. The fluid uptake value is defined as the greatest number of seconds required for the object to absorb either the first, second, or third insult. The exact method for determining fluid uptake values is explained in greater detail in connection with the examples.

Preferred absorbent garments according to the present invention may be different in size as indicated by reference to the surface area of one major planar surface of the garment. Nonetheless, the absorbent structures and containment means of the present invention may have a major planar surface defining a surface area which is small compared to the surface area of the absorbent garment. Generally, the ratio of the surface area of the absorbent structure or containment means to the surface area of the absorbent garment will be within the range of from about 8:10 to about 3:10, preferably within the range of from about 5:10 to about 3:10.

A wide variety of absorbent garments are known to those skilled in the art. The absorbent structures and containment means and superabsorbent material of the present invention can be incorporated into such known absorbent garments. Exemplary absorbent garments are generally described in U.S. Pat. No. 4,710,187 issued Dec. 1, 1987 to Boland et al.; 4,762,521 issued Aug. 9, 1988, to Roessler et al.; 4,770,656 issued Sep. 13, 1988, to Proxmire et al.; and 4,798,603 issued Jan. 17, 1989 to Meyer et al., which references are incorporated herein by reference.

As a general rule, the absorbent garments according to the present invention comprise a body-side liner adapted to contact the skin of the wearer, an outer cover superposed in facing relation with said liner, and an absorbent structure or containment means such as those described above superposed on said outer cover and located between the body-side liner and the outer cover.

In one preferred embodiment of the present invention, an absorbent garment is provided, which absorbent garment consists essentially of a body-sideliner, an outer cover, and an absorbent structure or containment means according to the present invention located between the body-side liner and the outer cover.

Those skilled in the art will recognize materials suitable for use as the body-side liner and outer cover. Exemplary of materials suitable for use as the body-side liner are spunbonded polypropylene or polyethylene having a basis weight of from about 15 to about 25 grams per square meter, and the like. Exemplary of material suitable for use as the outer cover are water-impervious materials such as polyolefin films, as well as water-pervious or water-pervious materials.

Turning now to the drawings, wherein FIG. 1 illustrates a disposable diaper 10 according to one embodiment of the present invention. Disposable diaper 10 includes an outer cover 12, a body-side liner 14, and an absorbent structure 16, located between the outer cover 12, and the body-side liner 14. Absorbent structure 16 is an absorbent structure according to the present invention. Specifically, in the illustrated embodiment absorbent structure 16 comprises a meltblown web of fibers which functions as the containment means which web contains superabsorbent material in an amount greater than 60 weight percent based on total weight of the containment means and superabsorbent material. As can be appreciated from reference to FIG. 1, the absorbent structure 16 has a relatively small surface area compared to the surface area of the entire disposable garment 10. Nonetheless, because absorbent structure 16 is formed in accordance with the present invention, the absorbent structure 16 and disposable garment 10 have fluid uptake values which render them suitable for use in the disposable garment 10.

Figure 2:
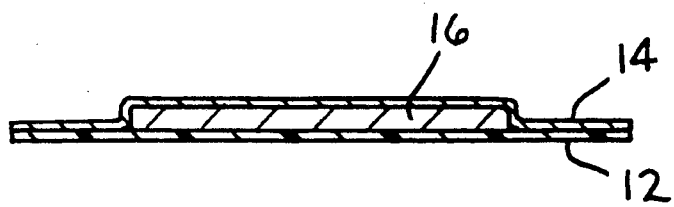
FIG. 2 is a cross-sectional view taken along line 2—2 of FIG. 1.

FIG. 2 is a cross-sectional view of FIG. 1 taken along line 2—2.

Figure 3:
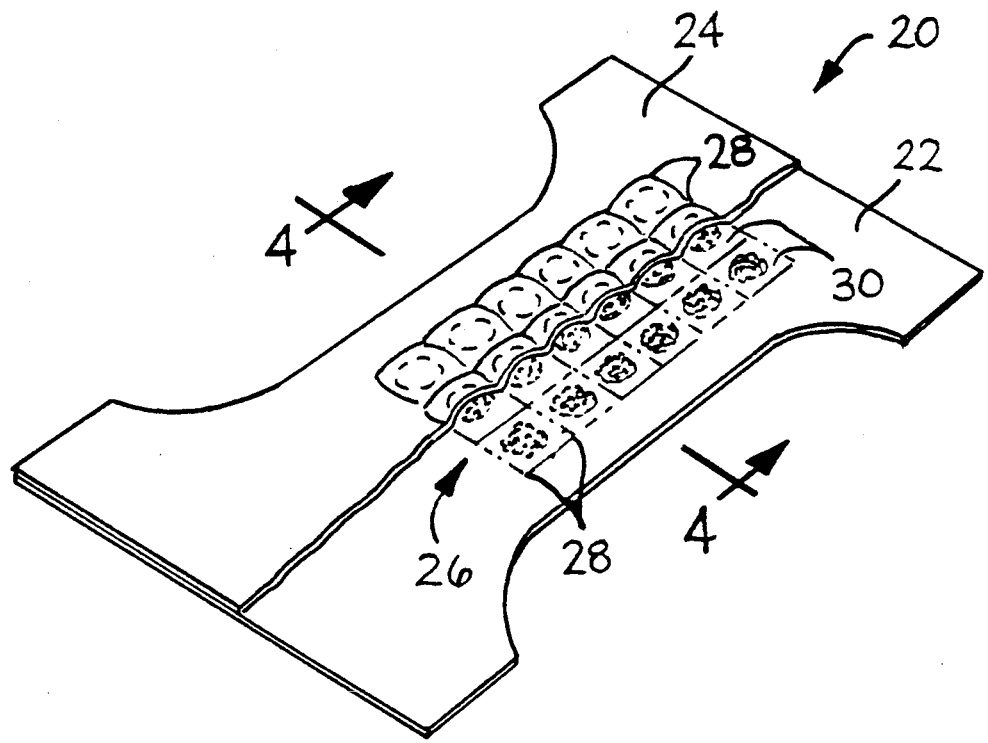
FIG. 3 is a perspective view of a second embodiment of a disposable diaper according to the present invention.

FIG. 3 illustrates another disposable diaper 20 according to the present invention. Disposable diaper 20 comprises an outer layer 22, and a body-side liner 24. Located between outer cover 22 and body-side liner 24 is an absorbent structure 26. In the embodiment illustrated in FIG. 3, absorbent structure 26 is formed by bonding outer cover 22 to body-side liner 24 along bond lines 28. In this manner, compartments 30 are formed, which compartments are capable of containing superabsorbent material 32. Again, as can be seen from reference to FIG. 3, the absorbent structure 26 has a relatively small surface area compared to the surface area of disposable diaper 20.

Figure 4:
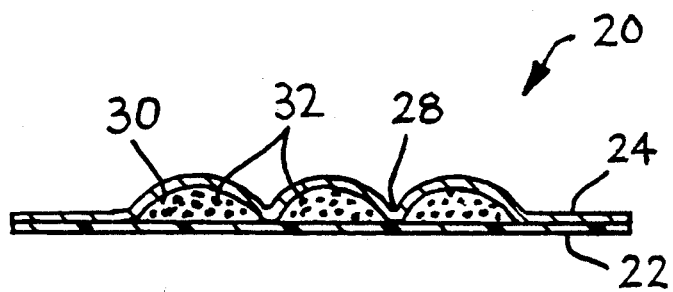
FIG. 4 is a cross-sectional view taken along line 4—4 of FIG. 3.

FIG. 4 is a cross-sectional view taken along line 4-of FIG. 3. FIG. 4 better illustrates how outer cover 22, body-side liner 24, and bond lines 28 cooperate to form compartments 30 for containing superabsorbent material 32.

The following test methods are employed in connection with the examples which follow:

TEST METHODS

Synthetic Urine

The synthetic urine composition referenced herein comprises 0.31 grams monobasic calcium phosphate monohydrate ($CaH_4(PO_4)_2H_2O$), 0.68 grams monobasic potassium phosphate ($KH_2PO_4$), 0.48 grams magnesium sulphate heptahydrate ($MgSO_4\,7H_2O$), 1.33 grams potassium sulphate ($K_2SO_4$), 1.24 grams tribasic sodium phosphate dodecahydrate ($Na_3PO_4\,12H_2O$), 4.4 grams sodium chloride (NaCl), 3.16 grams potassium chloride (KCl), 8.56 grams of urea ($CO(NH_2)_2$), 0.1 grams Pluronic 10R8 surfactant (a non-ionic surfactant commercially available from BASF-Wyandotte Corporation) and 1 gram methyl paraben and 1 gram Germall 115 preservative (commercially available from Santell Chemical Company, Chicago, Ill.) per liter using distilled water as the solvent. The components are added to 900 milliliters of distilled water in the order given and each dissolved before the next component is added. The solution is finally diluted to one liter.

Absorbency Under Load (AUL)

Figure 5:
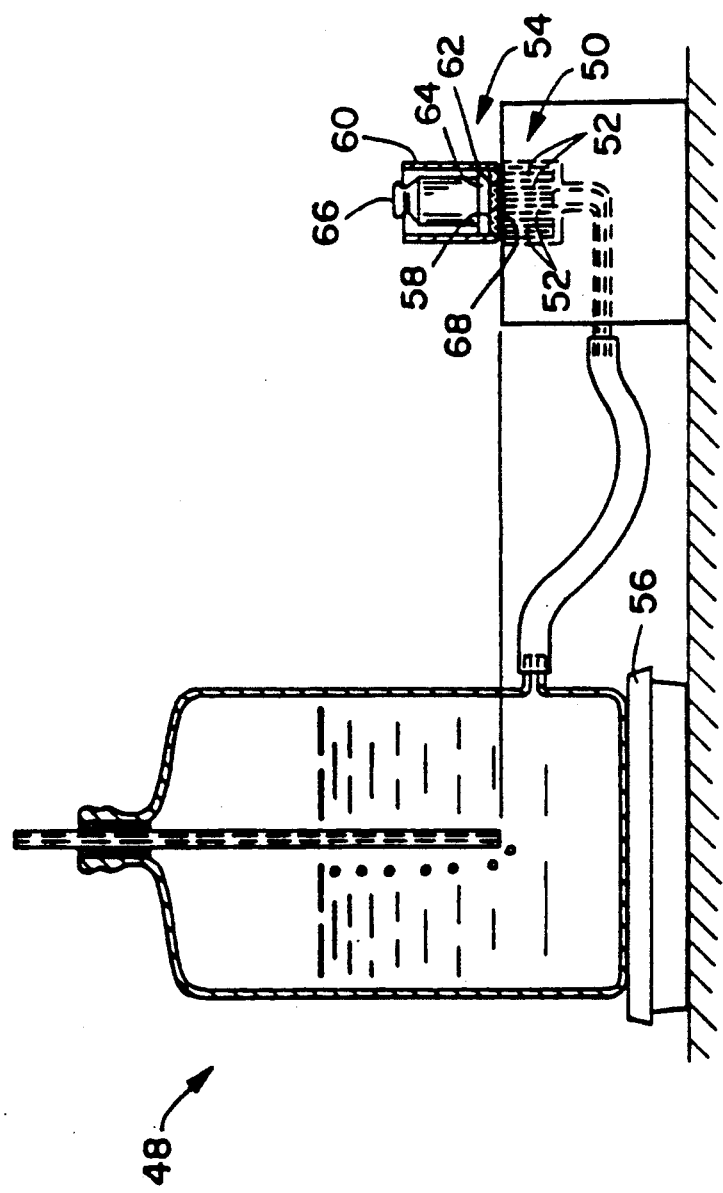
FIG. 5 is an illustration of the equipment employed in determining the absorbency under load (AUL) of superabsorbent material.

The ability of superabsorbent material to absorb a liquid while under load is determined as follows. Referring to FIG. 5, a demand absorbency tester (DAT) 48 is used, which is similar to a GATS (gravimetric absorbency test system), available from M/K Systems, Danners, Mass., as well as the system described by Lichstein at pages 129-142 of the INDA Technological Symposium Proceedings, March 1974. A porous plate 50 is used, having ports 52 confined within a 2.5 centimeter diameter area and covered by the absorbency under load (AUL) apparatus 54. An electrobalance 56 is used to measure the flow of fluid, into the superabsorbent particles 58. For this test, the fluid employed is an aqueous solution containing 0.9 weight percent sodium chloride, used at room temperature ($\sim 23°$ C.).

The special AUL apparatus 54 used to contain the superabsorbent particles comprises a cylinder 60 made from 1 inch (2.54 centimeters) inside diameter thermoplastic tubing which is machined-out slightly to be sure of concentricity. A 100 mesh stainless steel wire cloth 62 is fused on the bottom of cylinder 60 by heating the wire cloth in a flame until red hot, after which the cylinder is held onto the cloth until cooled. A soldering iron can be used to touch up the seal if unsuccessful or if it breaks. Care must be taken to maintain a flat, smooth bottom and not distort the inside of the cylinder. A 4.4 gram piston 64 is made from one inch diameter solid material (e.g., Plexiglas TM) and is machined to closely fit without binding in the cylinder 60. A standard 100 gram weight 66 is used to provide about 2 kilopascals (0.3 lbs per square inch) restraining load. A sample of superabsorbent particles weighing 0.16 grams is utilized for testing AUL. The sample is taken from granules which are pre-screened through U.S. Standard 30 mesh and retained on U.S. Standard 50 mesh (300 to 600 microns). The particles have a moisture content of less than about 5 weight percent.

This test is initiated by placing a three centimeter diameter GF/A glass filter paper 68 onto the plate 50. The paper is sized to be larger than the internal diameter and smaller than the outside diameter of the cylinder 60, to ensure good contact while eliminating evaporation over the ports 52 of the DAT 48 and then allowing saturation to occur. The particles 58 are weighed out on a weigh paper and placed on the wire cloth 62 at the bottom of the AUL apparatus 54. The apparatus 54 is shaken to level the particles 58 on the wire cloth 62. Care is taken to be sure no particles are clinging to the wall of the cylinder 60. After carefully placing, without pressing, the piston 64 and weight 66 on the particles 58 in the cylinder 60, the AUL apparatus 54 is placed on the glass filter paper 68. The amount of fluid picked-up is monitored as a function of time either directly by hand, with a strip-chart recorder or directly into a data acquisition or personal computer system.

The amount (in grams) of fluid picked-up after five-minutes divided by the weight of the sample (0.16 gram) is the AUL value in grams of picked-up fluid per gram of sample (g/g). The rate of fluid pick-up can also be measured. Two checks can be made to ensure the accuracy of the instantaneous final read-out. First, the height the piston 64 rises multiplied by the cross-sectional area of the cylinder 60 should nearly equal the amount of fluid picked up. Second, the AUL apparatus 54 can be weighed before and after the test, and the difference in weight should nearly equal the fluid picked up.

Free-Swell Rate

The free-swell rate for superabsorbent materials having a saturated retention capacity greater than 30 grams per gram is defined as the length of time in seconds required for one gram of superabsorbent material in particulate form, (which particles have a size within the range of from about 300 to about 600 microns, and a moisture content of less than 5 weight percent) to absorb 30 milliliters of a 0.9 weight percent aqueous sodium chloride solution, at room temperature ($-23°$ C.). The free-swell rate for a particular superabsorbent material is determined as follows. One gram of the superabsorbent material is spread out on the bottom of a plastic weighing boat (2 inch diameter at the bottom, 1 inch deep, and 3 inches by 3 inches square at the top) commercially available from Whitman Labsales Inc. catalogue number B8868. Thirty (30) milliliters of an aqueous solution containing 0.9 weight percent of sodium chloride is added to the weighing boat. The time for the superabsorbent material to absorb substantially all of the fluid, as indicated by the absence of pooled fluid, is recorded and reported as the free-swell rate.

For superabsorbent material having a saturated retention capacity of less than 30 grams per gram, the free-swell rate is defined as the length of time, in seconds, required for one gram of superabsorbent material in particulate form, (which particles have a size within the range of from about 300 to about 600 microns, and a moisture content of less than about 5 weight percent) to absorb an amount of an aqueous solution containing 0.9 weight percent of sodium chloride which amount is equal to the saturated retention capacity of the superabsorbent material. Thus, if a given superabsorbent material has a saturated retention capacity of 20 grams of fluid per gram of superabsorbent material, 20 grams of the described saline solution are employed to determine the free-swell rate of the superabsorbent material. The method used to determine the free-swell rate of such superabsorbent materials is the same as set forth above except that the described amount of fluid is used rather than 30 milliliters.

Saturated Retention Capacity

The saturated retention capacity is a measure of the total absorbent capacity of an absorbent garment, an absorbent structure, containment means and superabsorbent material, or a superabsorbent material. The saturated retention capacity is determined as follows. The material to be tested, having a moisture content of less than about 7 weight percent, is then weighed and submerged in an excess quantity of the room temperature ($\sim 23°$ C.) synthetic urine described above. The material is allowed to remain submerged for 20 minutes. After 20 minutes the material is removed from the urine and placed on a Teflon TM coated fiberglass screen having 0.25 inch openings (commercially available from Taconic Plastics Inc. Petersburg, N.Y.) which, in turn, is placed on a vacuum box and covered with a flexible rubber dam material. A vacuum of 3.5 kilopascals (0.5 pounds per square inch) is drawn in the vacuum box for a period of 5 minutes. The material is weighed. The amount of fluid retained by the material being tested is determined by subtracting the dry weight of the material from the wet weight of the material (after application of the vacuum) and is reported as the saturated retention capacity in grams of fluid retained. For relative comparisons, this value can be divided by the weight of the material to give the saturated retention capacity in grams of fluid retained per gram of tested material. If material, such as superabsorbent material or fiber, is drawn through the fiberglass screen while on the vacuum box, a screen having smaller openings should be used. Alternatively, a piece of the tea bag material described below can be placed between the material and the screen and the final value adjusted for the fluid retained by the material as described below.

When the material to be tested is superabsorbent material, the test is run as set forth above with the following exceptions. A bag is prepared from heat sealable tea bag material (grade 542, commercially available from the Kimberly-Clark Corporation). A six inch by three inch sample of the material is folded in half and heat sealed along two edges to form a generally square pouch. 0.2 grams of the superabsorbent material to be tested (in the form of particles having a size within the range of from about 300 to about 600 microns, and a moisture content of less than about 5 weight percent) is placed in the pouch and the third side is heat sealed. The test is performed as described with the amount of the fluid absorbed by the bag material being subtracted from the amount of fluid retained by the bag and superabsorbent material. The amount of fluid absorbed by the bag material is determined by performing the saturated retention capacity test on an empty bag.

Fluid Uptake Value

The fluid uptake value is defined as the greatest length of time (in seconds) required for an absorbent garment, absorbent structure or containment means and superabsorbent material to absorb any of three 100 milliliter insults (300 milliliters total) of room temperature ($\sim 23°$ C.) synthetic urine applied to material in a localized area (about 1 square centimeter) at a rate of 15 milliliters per second, with a period of about 5 minutes between each 100 milliliter insult. The time required to absorb each 100 milliliter insult is determined for each of the three insults, and the fluid uptake value is defined as the largest of the three values. The fluid uptake value is determined as follows. The object to be tested, having a moisture content of less than about 7 weight percent, is placed in a flat bottomed container. Three 100 milliliter insults of synthetic urine are applied to the object by delivery from a nozzle having a 4 millimeter diameter orifice. The nozzle is attached to a peristaltic pump equipped with a pulse suppressor. The nozzle is placed a distance of about 1 inch from the center of the object and the urine dispensed from the nozzle at an average rate of about 15 milliliters per second until 100 milliliters has been applied. After 5 minutes another 100 milliliters is applied. After 5 minutes a third 100 milliliter insult is applied. The nozzle forms an angle of about 60° from a generally horizontal major face of the object. The time for each 100 milliliter insult to be absorbed by the object is recorded. The highest of the three time periods for absorption is reported as the fluid uptake value (in seconds).

EXAMPLES

The following samples were employed in the examples and comparative examples.

Sample 1—A poly(acrylic acid) high-absorbency material commercially available from the Norsolor Company, France, under the trade designation Norsacryl A2 TM.

Sample 2—S starch grafted poly(acrylic acid) high-absorbency material commercially available from the Hoechst Celanese Company under the trade designation Sanwet TM IM 5600S.

Sample 3—A poly(acrylic acid) high-absorbency material commercially available from the Dow Chemical Company under the trade designation Drytech TM 533.

Sample 4—A poly(acrylic acid) high-absorbency material commercially available from the Dow Chemical Company under the trade designation Drytech TM 534.

Sample 5—Agglomerated fines of a poly(acrylic acid) high-absorbency material which fines are available from the Dow Chemical Company as the fines of Drytech TM 533, the fines are agglomerated according to copending U.S. patent application Ser. No. 07/304,616 filed Jan. 24, 1989, previously incorporated herein by reference.

Sample 6—A poly(acrylic acid) high-absorbency material commercially available from the Norsolor Chemical Company under the trade designation Norsacryl TM B41S.

Sample 7—Agglomerated fines of a poly(acrylic acid) high-absorbency material, which fines are available from the Dow Chemical Company as the fines of Drytech TM 533, the fines are agglomerated according to copending U.S. patent application Ser. No. 07/304,616 filed Jan. 24, 1989, previously incorporated herein by reference. The agglomerated fines are treated with a hydrophilizing agent after agglomeration.

Sample 8—Agglomerated fines of a poly(acrylic acid) high-absorbency material, which fines are available from the Dow Chemical Company under the trade designation Drytech TM 533, the fines are agglomerated according to copending U.S. patent application Ser. No. 07/304,616 filed Jan. 24, 1989, previously incorporated herein by reference. The fines are agglomerated in the presence of a hydrophilizing agent.

Sample 9—Agglomerated fines of a poly(acrylic acid) high-absorbency material, which fines are available from the Dow Chemical Company under the trade designation Drytech TM 533, the fines are agglomerated according to U.S. patent application Ser. No. 07/304,616 filed Jan. 24, 1989, previously incorporated herein by reference. The fines are agglomerated in the presence of a hydrophilizing agent.

EXAMPLE 1

Ten grams of a high-absorbency material selected from those described above is placed in the bottom of a polystyrene weighing dish commercially available from Whitman Labsales, Inc., catalogue number B-8870. The high-absorbency material is covered with a 200 gram per square meter meltblown fibrous web formed from a hydrophilic nylon copolymer which nylon copolymer is commercially available from Allied Signal, Inc., under the trade designation Hydrofil TM LCFX. The fibers of the meltblown web have a cross-sectional diameter greater than about 25 micrometers. The fluid uptake value of the described composite is then determined. The results of this determination as well as the free swell rate and five minute AUL of the high-absorbency materials employed are set forth in Table 1. The reported values represent the average of at least three repetitions.

TABLE 1

| Sample No. | Free Swell Rate | AUL | Fluid Uptake Value |
|---|---|---|---|
| 1* | 6 | 5 | 47 |
| 2* | 14 | 4 | 90 |
| 3* | 240 | 10 | 60 |
| 4* | 133 | 9 | 40 |
| 5 | 41 | 24 | 34 |
| 6 | 31 | 24 | 26 |
| 7 | 32 | 21 | 15 |
| 8 | 17 | 24 | 9 |
| 9 | 13 | 24 | 10 |

*Comparative Example

As can be seen from reference to Table 1, Sample Numbers 1-4 employ high absorbency materials with a five-minute AUL of less than 15 g/g and/or a free swell rate of greater than 60. It is seen that employing high absorbency material having a free swell rate greater than 60 and/or a five-minute AUL of less than 15 g/g produces a fluid uptake value of 40 or greater. Employing high-absorbency materials having a free swell rate of 60 or less and a five-minute AUL greater than 15 g/g produces absorbent composites having a fluid uptake value of 34 or less. Thus, it is seen that the combination of free swell rate and five-minute AUL required by some claims of the present invention produces an absorbent composite having an improved fluid uptake value when compared to the fluid uptake values of composites employing superabsorbent materials not having the required free swell rate and/or five-minute AUL.

EXAMPLE 2

Twelve grams of the high-absorbency material described as Sample Number 3 above, is placed between two 3 inch (7.6 centimeters) by 9 inch (22.9 centimeters) layers of the Hydrofil TM meltblown web employed in Example 1. The absorbent structure consisting of 12 grams of high absorbency material and two layers of Hydrofil TM meltblown web is then placed between two 4 inch by 10 inch layers of a 20 gram per square meter bilobal spunbonded polypropylene material. The bilobal polypropylene spunbonded material is then heat sealed around the periphery of the absorbent structure. The described structure is then placed in a six inch by nine inch by two inch dish. Three hundred milliliters of synthetic urine is then poured on the structure from a height of about 1 inch at a rate of about 11 milliliters per second. The synthetic urine is applied to the structure over substantially the entire upper surface of the structure in an attempt to compensate for the observed poor performance. The time required for the structure to imbibe the 300 milliliters of synthetic urine is recorded.

EXAMPLE 3

A structure as described in Example 2 is formed except that the high-absorbency material employed is that described as Sample Number 8 above. Additionally, due to the good performance of the absorbent structure, the synthetic urine is applied to the structure in a localized area rather than over the entire upper surface of said structure. Again, the time required for the structure to absorb the 300 milliliters of synthetic urine was recorded.

The results of the testing done in connection with Examples 2 and 3 is set forth in Table 2 which set follows.

TABLE 2

| Example Number | High Absorbency Material | Time to Imbibe |
|---|---|---|
| 2* | Sample Number 3 | >240 seconds |
| 3 | Sample Number 8 | 30 seconds |

*Comparative Example

As can be seen from reference to Table 2, the structure of Example Number 3 performs significantly better than the structure of Example Number 2. The improved performance results from the use of a high-absorbency material having a free swell rate of less than 60 seconds and a five-minute AUL of greater than 15 g/g.

EXAMPLE 4

A coformed web containing 76 weight percent of the high-absorbency material of Sample Number 3 and 24 weight percent of a fine fibered (less than about 5 micrometer diameter) meltblown Hydrofil ™ LCFX copolymer fibers is formed. The web has a basis weight of 850 grams per square meter. A 3 inch by 9 inch sample of the meltblown web is then covered on one surface with a 3 inch by 9 inch layer of the Hydrofil ™ meltblown web utilized in Examples 2 and 3. The absorbent structure thus formed is then placed between two layers of the 20 grams per square meter bilobal polypropylene spunbonded material employed in Example Numbers 2 and 3 with the spunbonded material being heat sealed around the periphery of the absorbent structure. The structure thus formed is subjected (with the Hydrofil ™ meltblown web facing up) to the same testing set forth in connection with Example 2 above.

EXAMPLE 5

An absorbent structure as described in Example 4 is prepared with the exception that the high-absorbency material employed is that material described as Sample Number 8 above. The absorbent structure so formed is subjected (with the Hydrofil ™ meltblown web facing up) to the same testing as set forth in connection with Example 3 above.

The results of the testing of Examples 4 and 5 are set forth in Table 3.

TABLE 3

| Example Number | High Absorbency Material | Time to Imbibe |
|---|---|---|
| 4* | Sample Number 3 | >240 seconds |
| 5 | Sample Number 8 | 31 seconds |

*Comparative Example

As can be seen by reference to Table 3, Example Number 5 performed significantly better than Example Number 4. Again, the superior performance results from the careful selection of a high-absorbency material having a free swell rate of less than 60 and a five-minute AUL greater than 15 g/g.

EXAMPLE 6

The high-absorbency material described as Sample Number 5 above is formed into a coformed web containing about 76 weight percent of the high-absorbency material and about 24 weight percent of meltblown fine fibers (diameter of less than about 5 micrometers) of a Hydrofil ™ LCFX copolymer. 12 centimeter by 12 centimeter webs of this material are cut from the coformed webs which have a basis weight of about 850 grams per square meter and a density of about 0.22 gram per cubic centimeter. One half of the webs are compressed in a flat platen press to a density of about 0.33 gram per cubic centimeter. The webs are then subjected to fluid uptake value determinations. The results of this testing are set forth in Table 4 which follows.

TABLE 4

| | Dry Volume (cm³) | Fluid Uptake Value[1] |
|---|---|---|
| Compressed | 35 | 26.5 |
| Uncompressed | 55 | 27.5 |

[1]Average of two repetitions

As can be seen from reference to Table 4, compression of a meltblown web containing the described high-absorbency material does not appear to significantly affect the fluid uptake value of the meltblown web.

EXAMPLE 7

The high-absorbency material described as Sample Number 3 above is air laid with wood pulp fluff according to the teachings of U.S. Pat. No. 4,699,823 issued Oct. 13, 1987, to Kellenberger, et al. which is hereby incorporated by reference. The air laid batt thus formed is incorporated into disposable infant diapers according to the teachings of U.S. Pat. No. 4,798,603, issued Jan. 17, 1989, and previously incorporated herein by reference. The diapers comprise a water impervious outer cover sheet, the absorbent air laid batts of high absorbency material and wood pulp fluff, a creped wadding tissue wrap surrounding the air laid batts, a transfer layer and a body-side liner. Specifically, the air laid batts of wood pulp fluff and high absorbency material are incorporated into disposable diapers commercially marketed by the Kimberly-Clark Corporation under the trade name HUGGIES ® Supertrim Medium Disposable Diapers.

The diapers so produced are subjected to a local use test. According to the local use test, each of 100 babies are provided with ten of the described diapers. The diapers are used on the babies, then those diapers containing only urine are returned for evaluation. About 700 diapers are returned. For each of the diapers used, the individual applying and removing the diaper is asked to indicate whether there is leakage from the diaper. Additionally, the person removing the diaper is asked to evaluate the relative dryness (skin wetness rating) of the baby's skin in the perineal region on a scale from 0 to 5, where 0 is dry skin, 1 is slightly damp, 2 is damp, 3 is wet, 4 is very wet, and 5 is soaked. The percent leaks and average skin wetness rating as well as the exact composition of the air laid web of wood pulp fluff and high absorbency material is set forth in Table 5.

EXAMPLES 8 AND 9

Disposable diapers are prepared as set forth in Example 7 above with the exception that Example 8 employs the high-absorbency material described as Sample Number 5 above and Example 9 employs the high-absorbency material described as Sample Number 8 above. The diapers are prepared and tested as set forth in Example 7. The results of the testing and the composition of the diapers are set forth in Table 5 which follows.

TABLE 5

| Example Number | High Absorbency Material | Weight of[1] Fluff (g) | Conc. of[2] H.A.M. | Percent Leaks | Avg. Skin Wetness Rating |
| --- | --- | --- | --- | --- | --- |
| 7* | Sample Number 3 | 26 | 16 | 10.4 | 0.81 |
| 7* | Sample Number 3 | 26 | 20 | 8.5 | 0.75 |
| 8* | Sample Number 5 | 26 | 16 | 12.0 | 0.86 |
| 8* | Sample Number 5 | 26 | 20 | 10.8 | 0.79 |
| 9* | Sample Number 8 | 26 | 16 | 13.9 | 0.86 |
| 9* | Sample Number 8 | 26 | 20 | 11.5 | 0.78 |

*Comparative Example
[1]Weight of wood pulp fluff in grams
[2]Concentration of high absorbency material in weight percent based on total weight of fluff and high absorbency material As can be seen from reference to Table 5, and comparison of Example Number 7 with Example Numbers 8 and 9, the use of high-absorbency materials having a free swell rate of less than 60 and an AUL greater than 15 g/g (Example Numbers 8 and 9) does not bring a significant benefit to the disposable diaper when the high-absorbency material is employed at low concentrations in hydrophilic fibers.

EXAMPLE 10

An infant diaper commercially available from the Kimberly-Clark Corporation under the trade designation Huggies® Supertrim Disposable Diapers (medium) is provided. The diaper comprises an outer cover, a tissue wrapped airlaid batt of wood pulp fluff and the high-absorbency material of Sample 4, a transfer layer, and a body-side liner as described in U.S. Pat. No. 4,798,603 issued Jan. 17, 1989 to Meyer et al. The transfer layer and the body-side liner are removed from the diaper and replaced with a Guilford Warp Knit Fabric commercially available from Guilford Mills, Greensborough, N.C., under the trade designation Style 19903.

The diapers are subjected to a local use test. According to the local use test, each of 20 "heavy wetter" (average at least about 200 grams of urine per night) babies are provided with two of the described diapers (40 total). The diapers are used overnight on the babies and the used diapers are returned for evaluation. About 37 diapers are evaluated. For each of the diapers used, the individual applying and removing the diaper is asked to indicate whether there is leakage from the diaper. Additionally, the person removing the diaper is asked to evaluate the relative dryness (skin wetness rating) of the baby's skin in the perineal region on a scale from 0 to 5, where 0 is dry skin, 1 is slightly damp, 2 is damp, 3 is wet, 4 is very wet, and 5 is soaked. The percent leaks and average skin wetness rating as well as the exact composition of the diaper is set forth in Table 6.

EXAMPLE 11

A diaper as described in Example 10 is provided. The tissue wrapped absorbent core, transfer layer and body-side liner are removed. The absorbent core is replaced with a 125 grams per square meter coform material formed from 70 weight percent wood pulp fluff and 30 weight percent meltblown polypropylene fibers which material is treated with Triton X-102 a surfactant commercially available from the Rohm & Hass Company. On top of the coform material is longitudinally placed a 4 inch by about 9 inch meltblown, tissue-wrapped web containing 76 weight percent of the high absorbency material of sample 4 and 24 weight percent of fine meltblown fibers of a Hydrofil TM copolymer. Prior to being placed on the coform material, the meltblown, tissue-wrapped web is humidified for about 14 hours at 100° C. and 80% relative humidity pressed in a flat platen press under a load of about 20 kilopascals (140 pounds per square inch) for about 15 seconds and dried for about 2 hours at 135° F. at ambient relative humidity. The liner material of example 10 is then placed over the absorbent structure. The diaper so formed is subjected to a local use test as set forth in example 10. The results are set forth in Table 6.

EXAMPLE 12

A diaper as described in example 11 is prepared except that the high-absorbency material employed is that of sample no. 5 described above. The diaper is subjected to the local use test as described in example 10. The results are set forth in Table 6.

TABLE 6

| Example Number | Wood Pulp Fluff/HAM[1] | | | Meltblown Web[5] | | | Coform Web[6] | | | Percent Leaks | Avg. Skin Wetness Rating |
| --- | --- | --- | --- | --- | --- | --- | --- | --- | --- | --- | --- |
| | SRC[2] | Vol.[3] | HAM[4] | SRC[2] | Vol.[3] | HAM[4] | SRC[2] | Vol.[3] | Wt[7] | | |
| 10* | 500 | 350 | 4.5 | — | — | — | — | — | — | 26 | 1.05 |
| 11 | — | — | — | 370 | 55 | 15 | 110 | 97 | 9 | 33 | 0.78 |
| 12 | — | — | — | 370 | 55 | 15 | 110 | 97 | 9 | 18 | 0.74 |

*Not an example of the present invention
[1]Airlaid batt of wood pulp fluff and the high-absorbency material
[2]Saturated retention capacity in grams
[3]Dry volume in cubic centimeters
[4]Weight (in grams) of high-absorbency material present
[5]Meltblown web, 76% high absorbency material, 24% meltblown nylon copolymer fibers
[6]Coform web, 70% wood pulp fluff, 30% polypropylene fibers
[7]Weight (in grams) of coform web As can be seen from reference to examples 11 and 12, diapers having an absorbent structure with a small volume (about 55 cubic centimeters) can be produced which generally meet or exceed the performance characteristics of conventional, known diapers (example 10). Moreover, comparison of examples 11 and 12 indicates that the use of a high-absorbency material having a free-swell rate of less than 60 seconds and a five-minute AUL of at least about 15 g/g (example 12) produces a diaper having improved performance compared to a similar diaper employing a high-absorbency material not meeting such limitations (example 11).

APPENDIX A

EXAMPLE A-1

In a one liter reactor 80 grams of Drytech ® (The Dow Chemical Company) polymer (sodium polyacrylate) having mixed particle size distribution is mixed with 300 grams of Isopar M hydrocarbon (deodorized kerosene by Exxon). The dispersion is suspended using agitation. The monomer phase is prepared with a solution of 12 grams of acrylic acid; 0.05 grams of trimethylolpropane triacrylate; 0.05 grams of a chelating agent; 15.7 grams of water; 12 grams of a 50 percent solution of sodium hydroxide; and 0.1 grams of Isopar M hydrocarbon and 0.25 grams of hydrophobic fumes silica sold as Aerosil ® R-972 by Degussa. The aggregates or clusters are formed by adding the monomer phase to the reactor under constant agitation at 600 rpm, 20° C. and under the flow of sulphur dioxide gas between 0.1 to 10.0 ppm/min. The aggregates are then separated from the hydrocarbon by filtration and then dried in a hot air oven at 100° C. overnight.

EXAMPLE A-2

Polymer particles having a mixed particle size are aggregated similarly to those polymers in Example A-1. However, the aggregates are prepared without the acrylic acid in the monomer phase and the amount of hydrophobic fumed silica used in the process is one gram. Thirty grams of the aggregates are then treated with a wetting agent by adding 5 grams of a 0.4 percent Voranol ® (polyol of The Dow Chemical Company) in water solution. The aggregates are then dried in an oven.

EXAMPLE A-3

In a 50-gallon (189.3 liters) reactor 50 pounds (22.7 kg) of Drytech ® (The Dow Chemical Company) polymer having a particle size of smaller than 80 mesh (177 micrometers) is mixed with 160 pounds (72.7 kg) of Isopar L hydrocarbon. The dispersion is suspended using agitation. The monomer phase is prepared with a solution of 3405 grams of acrylic acid; 14 grams of trimethylolpropane triacrylate; 14 grams of a chelating agent, 4313 grams of water; 3405 grams of a 50 percent solution of sodium hydroxide; and 14 grams of t-butyl hydrogen peroxide, suspended as droplets in a solution of 25 pounds of Isopar M hydrocarbon and 140 grams of hydrophobic fumes silica sold as Aerosil ® R-974 by Degussa. The aggregates are formed by adding the monomer phase to the reactor under constant agitation then allowing polymerization to occur at 20° C. for an hour, the reactor is vacuum stripped to 90° C. and is cooled to 70° C. A solution of 20 grams of persulfate, 140 grams of Voranol ® and 4400 grams of water is then added to the aggregates at 70° C. for 90 minutes. The aggregates are then vacuum stripped and separated from the hydrocarbon by filtration and then dried in a hot air oven at 100° C. overnight.

What is claimed is:

1. An absorbent structure, said absorbent structure comprising:
   means for containing a superabsorbent material; and
   a superabsorbent material contained by said containment means, said superabsorbent material having a free-swell rate of less than about 60 seconds and a five-minute AUL of at least about 15 g/g, said superabsorbent being present in said containment means in an amount of from about 60 to about 100 weight percent, based on a total weight of said containment means and said superabsorbent material.

2. The absorbent structure according to claim 1 wherein said containment means comprises a fibrous matrix.

3. The absorbent structure according to claim 2 wherein said fibrous matrix is formed from a hydrophilic polymeric material.

4. The absorbent structure according to claim 3 wherein said fibrous matrix comprises less than about 10 weight percent of cellulosic fibers.

5. The absorbent structure according to claim 1 wherein said containment means comprises two layers of material, at least one layer being water-pervious, and wherein said superabsorbent material is located between said two layers of material.

6. The absorbent structure according to claim 1 wherein the superabsorbent material has a free-swell rate of less than about 40 seconds.

7. The absorbent structure according to claim 1 wherein the superabsorbent material has a free-swell rate of less than about 30 seconds.

8. The absorbent structure according to claim 1 wherein said superabsorbent material has a five-minute AUL of at least about 18 g/g.

9. The absorbent structure according to claim 8 wherein said superabsorbent material has a five-minute AUL of at least about 21 g/g.

10. The absorbent structure according to claim 1 wherein said superabsorbent material comprises generally non-friable particles of agglomerated fines of a water-swellable, substantially water-insoluble polyacrylic acid.

11. The absorbent structure according to claim wherein said absorbent structure has an average thickness of less than about 0.2 inches.

12. The absorbent structure according to claim 11 wherein said absorbent structure has a fluid uptake value of less than about 30 seconds.

13. The absorbent structure according to claim 12 wherein said superabsorbent material is present in said containment means in an amount of from about 70 to about 100 weight percent based on total weight of said containment means and said superabsorbent material.

14. An absorbent garment, said garment comprising:
   an outer cover; and
   an absorbent structure superposed on said outer cover, said absorbent structure comprising:
     means for containing a superabsorbent material; and
     a superabsorbent material contained by said containment means, said superabsorbent material having a free-swell rate of less than about 60 seconds and a five-minute AUL of at least about 15 g/g, said superabsorbent being present in said containment means in an amount of from about 60 to about 100 weight percent, based on a total weight of said containment means and said superabsorbent material.

15. The absorbent garment according to claim 14 wherein said containment means comprises a fibrous matrix.

16. The absorbent garment according to claim 15 wherein said fibrous matrix is formed from a hydrophilic polymeric material.

17. The absorbent garment according to claim 16 wherein said fibrous matrix comprises less than about 10 weight percent cellulosic fibers.

18. The absorbent garment according to claim 14 wherein said containment means comprises two layers of material, at least one layer being water-pervious, and wherein said superabsorbent material is located between said two layers of material.

19. The absorbent garment according to claim 14 wherein the superabsorbent material has a free-swell rate of less than about 40 seconds.

20. The absorbent garment according to claim 14 wherein the superabsorbent material has a free-swell rate of less than about 30 seconds.

21. The absorbent garment according to claim 14 wherein said superabsorbent material has a five-minute AUL of at least about 18 g/g.

22. The absorbent garment according to claim 21 wherein said superabsorbent material has a five-minute AUL of at least about 21 g/g.

23. The absorbent garment according to claim 14 wherein said superabsorbent material comprises generally non-friable particles of agglomerated fines of a water-swellable, substantially water-insoluble polyacrylic acid.

24. The absorbent garment according to claim 14 wherein said absorbent garment has an average thickness of less than about 0.25 inches.

25. The absorbent garment according to claim 24 wherein said absorbent garment has an average thickness of less than about 0.20 inches.

26. The absorbent garment according to claim 14 wherein said absorbent garment has a fluid uptake value of less than about 30 seconds.

27. The absorbent garment according to claim 14 wherein said superabsorbent material is present in said containment means in an amount of from about 70 to about 100 weight percent based on total weight of said containment means and said superabsorbent material.

28. The absorbent garment according to claim 14, wherein the ratio of the surface area of the absorbent structure to the surface area of the absorbent garment is within the range of from about 3:10 to about 8:10.

29. The absorbent garment according to claim 14 further comprising a body-side liner, said absorbent structure being located between said body-side liner and said outer cover.

30. A thin, disposable diaper, said diaper comprising:
a body-side liner;
an outer cover superposed in facing relation with said liner; and
an absorbent structure located between said liner and outer cover, said absorbent structure comprising:
means for containing a superabsorbent material; and
superabsorbent material contained by said containment means, said superabsorbent material having a free-swell rate of less than about 60 seconds and a five-minute AUL of at least about 15 g/g, said superabsorbent being present in said containment means in an amount of from about 60 to about 100 weight percent, based on a total weight of said containment means and said superabsorbent material; said absorbent garment having an average thickness of less than about 0.25 inches.

31. The disposable diaper according to claim 30 wherein said diaper consists essentially of said body-side liner, said outer cover, and said absorbent structure.

32. The disposable diaper according to claim 30 wherein said diaper cover is water-pervious.

33. The diaper according to claim 30 wherein said superabsorbent material is present in said containment means in an amount of from about 70 to about 100 weight percent based on total weight of said containment means and said superabsorbent material.

34. The diaper according to claim 30 wherein said diaper has an average thickness of less than about 0.20 inches.

35. An absorbent garment, said absorbent garment comprising:
means for containing a superabsorbent material; and
superabsorbent material contained by said means, said superabsorbent material being present in said containment means in an amount of from about 60 to about 100 weight percent, based on the total weight of the containment means and said superabsorbent material, said containment means and superabsorbent material defining a dry volume of less than about 180 cubic centimeters, said absorbent garment having a saturated retention capacity of at least about 2 times the dry volume of said containment means and superabsorbent material with the containment means and superabsorbent material accounting for at least about 60 volume percent of said saturated retention capacity of said absorbent garment.

36. The absorbent garment according to claim 35 wherein said containment means comprises a fibrous matrix.

37. The absorbent garment according to claim 36 wherein said fibrous matrix is formed from a hydrophilic polymeric material.

38. The absorbent garment according to claim 37 wherein said fibrous matrix comprises less than about 10 weight percent cellulosic fibers.

39. The absorbent garment according to claim 35 wherein said containment means comprises two layers of material, at least one layer being water-pervious, and wherein said superabsorbent material is located between said two layers of material.

40. The absorbent garment according to claim 39 wherein said two layers form a compartment in which the superabsorbent material is contained.

41. The absorbent garment according to claim 35 wherein said superabsorbent material comprises generally non-friable particles of agglomerated fines of a water-swellable, substantially water-insoluble polyacrylic acid.

42. The absorbent garment according to claim 35 wherein said absorbent garment has an average thickness of less than about 0.25 inches.

43. The absorbent garment according to claim 42 wherein said absorbent garment has an average thickness of less than about 0.20 inches.

44. The absorbent garment according to claim 35 wherein said absorbent garment has a fluid uptake value of less than about 30 seconds.

45. The absorbent garment according to claim 44 wherein said absorbent garment has a fluid uptake value of less than about 20 seconds.

46. The absorbent garment according to claim 35 wherein said superabsorbent material is present in said containment means in an amount of from about 70 to about 100 weight percent based on total weight of said containment means and said superabsorbent material.

47. The absorbent garment according to claim 35 further comprising a body-side liner and an outer cover, said containment means being located between said body-side liner and said outer cover.

48. The absorbent garment according to claim 35 wherein the dry volume of the containment means and superabsorbent material is less than about 150 cubic centimeters.

49. The absorbent garment according to claim 48 wherein the dry volume of the containment means and superabsorbent material is less than about 120 cubic centimeters.

50. The absorbent garment according to claim 49 wherein the dry volume of the containment means and superabsorbent material is less than about 100 cubic centimeters.

51. The absorbent garment according to claim 35 wherein the absorbent garment has a saturated retention capacity of at least about 3 times the dry volume of the containment means and superabsorbent material.

52. The absorbent garment according to claim 51 wherein the absorbent garment has a saturated retention capacity of at least about 5 times the dry volume of the containment means and superabsorbent material.

53. The absorbent garment according to claim 35 wherein the containment means and superabsorbent material accounts for at least about 75 volume percent of the saturated retention capacity of said absorbent garment.

54. The absorbent garment according to claim 53 wherein the containment means and superabsorbent material accounts for at least about 85 volume percent of the saturated retention capacity of said absorbent garment.

55. A thin disposable diaper, said diaper consisting essentially of:
   a body-side liner;
   an outer cover superposed in facing relation with said liner;
   means for containing a superabsorbent material said means being located between said liner and outer cover; and
   superabsorbent material contained by said containment means, said superabsorbent material being present in said containment means in an amount of from about 60 to about 100 weight percent based on a total weight of the containment means and superabsorbent material, said containment means and superabsorbent material having an average thickness of less than about 0.2 inch, said diaper having a saturated retention capacity of at least about 300 grams.

56. The diaper according to claim 55 wherein said containment means and superabsorbent material has an average thickness of less than about 0.18 inch.

57. The diaper according to claim 55 wherein said containment means and superabsorbent material defines a dry volume of less than about 180 cubic centimeters.

58. The absorbent structure according to claim 1 wherein said superabsorbent material is present in said containment means in an amount of from about 70 to about 100 weight percent, based on the total weight of said containment means and said superabsorbent material.

* * * * *

UNITED STATES PATENT AND TRADEMARK OFFICE
CERTIFICATE OF CORRECTION

PATENT NO. : 5,149,335
DATED : September 22, 1992
INVENTOR(S) : Stanley R. Kellenberger; Wen-Huey Shih-Schroeder; Anthony J. Wisneski It is certified that error appears in the above-identified patent and that said Letters Patent is hereby corrected as shown below:

Column 1, Line 28, delete the number "4,076,63" and substitute therefor --4,076,663--.

Column 4, Line 54, delete the word "Wall" and substitute therefor --Waal--.

Column 17, Line 25, delete "(-23° C.)" and substitute therefor --(~23° C.)--.

Column 24, Line 33, delete the letter "C" and substitute therefor --F--.

Signed and Sealed this

Twenty-eighth Day of December, 1993

Attest:

BRUCE LEHMAN

Attesting Officer

Commissioner of Patents and Trademarks